(12) United States Patent
Harriman et al.

(10) Patent No.: US 12,102,070 B2
(45) Date of Patent: Oct. 1, 2024

(54) CAMELIZATION OF A HUMAN VARIABLE DOMAIN BY GENE CONVERSION

(71) Applicant: Crystal Bioscience Inc., San Diego, CA (US)

(72) Inventors: William Don Harriman, Alameda, CA (US); Philip A. Leighton, San Francisco, CA (US)

(73) Assignee: CRYSTAL BIOSCIENCE INC., Emeryville, CA (US)

( * ) Notice: Subject to any disclaimer, the term of this patent is extended or adjusted under 35 U.S.C. 154(b) by 964 days.

(21) Appl. No.: 15/734,534

(22) PCT Filed: Jun. 5, 2019

(86) PCT No.: PCT/US2019/035525
§ 371 (c)(1),
(2) Date: Dec. 2, 2020

(87) PCT Pub. No.: WO2019/240999
PCT Pub. Date: Dec. 19, 2019

(65) Prior Publication Data
US 2021/0230629 A1    Jul. 29, 2021

Related U.S. Application Data (60) Provisional application No. 62/684,629, filed on Jun. 13, 2018.

(51) Int. Cl.
*A01K 67/0278* (2024.01)
*A01K 67/0275* (2024.01)
*C07K 16/46* (2006.01)
*C12N 15/85* (2006.01)

(52) U.S. Cl.
CPC ...... *A01K 67/0278* (2013.01); *A01K 67/0275* (2013.01); *C07K 16/462* (2013.01); *C12N 15/8509* (2013.01); *A01K 2227/30* (2013.01); *A01K 2267/01* (2013.01); *C07K 2317/22* (2013.01)

(58) Field of Classification Search
CPC .......... A01K 67/0278; A01K 67/0275; A01K 2227/30; A01K 2267/01; C07K 16/462; C07K 2317/22; C12N 15/8509
USPC .................... 800/19, 6; 530/387.3
See application file for complete search history.

(56) References Cited

U.S. PATENT DOCUMENTS

| | | | |
|---|---|---|---|
| 2009/0098134 A1* | 4/2009 | Buelow | C07K 16/00 800/19 |
| 2011/0145937 A1* | 6/2011 | MacDonald | C07K 16/462 800/18 |
| 2015/0210776 A1 | 7/2015 | Macdonald et al. | |
| 2016/0280795 A1 | 9/2016 | Wang | |
| 2016/0304585 A1* | 10/2016 | Harriman | A01K 67/0275 |
| 2021/0332129 A1* | 10/2021 | Hashimoto | C12N 15/09 |

OTHER PUBLICATIONS

Davies et al., "Camelising' human antibody fragments: NMR studies on VH domains", FEBS Letters, 1994, 339: 285-290.

* cited by examiner

*Primary Examiner* — Anne Marie S Wehbe
(74) *Attorney, Agent, or Firm* — James S. Keddie; Bozicevic, Field & Francis LLP (57) ABSTRACT

This disclosure provides, among other things, a transgenic animal that uses gene conversion for antibody diversification comprising B cells in which the endogenous immunoglobulin heavy chain locus comprises: (a) a functional immunoglobulin heavy chain gene comprising a nucleic acid encoding a human heavy chain variable domain; and (b) a plurality of pseudogenes that are operably linked to the functional immunoglobulin heavy chain gene and that donate, by gene conversion, nucleotide sequence to the nucleic acid encoding the human heavy chain variable domain of (a), wherein the pseudogenes are upstream or downstream of the functional immunoglobulin heavy chain gene and encode variable domains that have camelizing amino acid substitutions.

18 Claims, 3 Drawing Sheets

CAMELIZATION OF A HUMAN VARIABLE DOMAIN BY GENE CONVERSION

CROSS-REFERENCING

This application is the national phase under 35 U.S.C. § 371 of International Application No. PCT/US2019/035525, filed on Jun. 5, 2019, which claims the benefit of U.S. provisional application Ser. No. 62/684,629, filed on Jun. 13, 2018, which applications are incorporated herein by reference.

BACKGROUND

Heavy chain-only antibodies can be expressed in the absence of light chain and therefore have what can be referred to as an autonomous heavy chain. An autonomous heavy chain variable domain (VH) can fold and bind to antigens autonomously, i.e., without aggregating and without the requirement of variable light chain (VL). Strategies for producing antibodies that comprise an autonomous heavy chain variable domain are reviewed in Janssens et al (Proc. Natl. Acad. Sci. 2006 103:15130-5), Brüggemann et al (Crit. Rev. Immunol. 2006 26:377-90), Zou et al (J. Immunol. 2005 175:3769-79) and Nguyen et al (Immunology 2003 109:93-101), for example.

One challenge in producing heavy chain-only antibodies is how to efficiently produce such antibodies using the immune system of the host animal.

Certain aspects of this disclosure relate to a transgenic animal that produces heavy chain-only antibodies via gene conversion.

SUMMARY

This disclosure provides, among other things, a transgenic animal that uses gene conversion for antibody diversification comprising B cells in which the endogenous immunoglobulin heavy chain locus comprises: (a) a functional immunoglobulin heavy chain gene comprising a nucleic acid encoding a human heavy chain variable domain; and (b) a plurality of pseudogenes that are operably linked to the functional immunoglobulin heavy chain gene and that donate, by gene conversion, nucleotide sequence to the nucleic acid encoding the human heavy chain variable domain of (a), wherein the pseudogenes are upstream or downstream of the functional immunoglobulin heavy chain gene and encode variable domains that have camelizing amino acid substitutions.

In such animals, the nucleic acid encoding the human heavy chain variable domain may mutate via gene conversion with the pseudogenes, resulting in the production of a camelized human immunoglobulin heavy chain.

BRIEF DESCRIPTION OF THE DRAWINGS

The skilled artisan will understand that the drawings, described below, are for illustration purposes only. The drawings are not intended to limit the scope of the present teachings in any way.

DEFINITIONS

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. "Unlinked" means that the associated genetic elements are not closely associated with one another and the function of one does not affect the other.

The term "homozygous" indicates that identical alleles reside at the same loci on homologous chromosomes. In contrast, "heterozygous" indicates that different alleles reside at the same loci on homologous chromosomes. A transgenic animal may be homozygous for a transgene, or hemizygous for a transgene if there is no counterpart at the same locus on the homologous chromosome.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introducing" in the context of inserting a nucleic acid sequence into a cell, includes "transfection" and "transformation" and all other methods of introducing a nucleic acid into a cell, where the nucleic acid sequence may be incorporated into the genome of the cell (e.g., chromosome, plasmid, plastid, or mitochondrial DNA) or converted into an autonomous replicon, or transiently expressed.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The term "replacing", in the context of replacing one genetic locus with another, refers to a single step protocol or multiple step protocol.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "isolated", with respect to a cell, refers to a cell that is cultured in vitro. If an animal is described as containing isolated cells, then those isolated cells were cultured in vitro and then implanted into the animal.

The term "progeny" or "off-spring" refers to any and all future generations derived and descending from a particular animal or cell. Thus, the progeny an animal of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell. A chimeric animal may have cells donated by another animal in the germline, in which case the progeny of the animal may be heterozygous for chromosomes in the donated cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The phrases "hybrid animal", "transgenic hybrid animal" and the like are used interchangeably herein to mean an animal obtained from the mating of a first animal having certain qualities with a second animal having certain qualities. For example, a hybrid animal of the present disclosure can refer to the transgenic progeny obtained from the mating of a transgenic first animal that produces a common light-chain with a second transgenic animal that produces a synthetic heavy-chain. A hybrid animal can be immunized and used as a source for the production of antigen-specific antibodies.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F (ab') 2, and or other antibody fragments that retain specific binding to antigen, and monoclonal antibodies.

Antibodies may exist in a variety of other forms including, for example, Fv, Fab, and (Fab') 2, as well as bi-functional (i.e. bispecific) hybrid antibodies (e.g., Lanzavecchia and Scheidegger, Eur. J. Immunol. 1987, 17 (1): 105-111) and in single chains (e.g., Huston et al., Proc. Natl. Acad. Sci. U.S.A 1988, 85 (16): 5879-5883 and Bird et al., Science. 1988, 242 (4877): 423-426, which are incorporated herein by reference). (See, generally, Hood et al., "Immunology", Benjamin, N.Y., 2nd ed. 1984, and Hunkapiller and Hood, Nature. 1986, 323 (6083): 15-16).

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. In the context of the heavy and light chain immunoglobulin loci, pseudogenes do not contain promoter regions, recombination signal sequences or leader sequences.

The terms "upstream" and "downstream" are used with reference to the direction of transcription.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and analyte when they are specifically bound in an antibody/analyte complex is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M or less.

A "variable region" of a heavy or light antibody chain is an N-terminal mature domain of the chain that contains CDR1, CDR2 and CD3, and framework regions (where CDR refers to "complementarity determining region"). The heavy and light chain of an antibody both contains a variable domain. All domains, CDRs and residue numbers are assigned on the basis of sequence alignments and structural knowledge. Identification and numbering of framework and CDR residues is as described in by Chothia et al. and others (Chotia et al., J. Mol. Biol. 1998, 278 (2): 457-479).

VH is the variable domain of an antibody heavy chain. VL is the variable domain of an antibody light chain.

The terms "gene" and "locus" are used interchangeably herein. Neither term implies that a gene is actively transcribed or intact. Both terms encompass genes that have been inactivated.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "genetically linked" refers to two genetic elements that exist on the same chromosome such that there is a tendency for the genetic elements to be inherited together during meiosis (i.e., the elements have a recombination frequency of less than 50%, less than 40%, less than 30%, less than 20%, less than 10% or less than 5%). Two genetic elements that are linked closely to each other are less likely to be separated onto different chromatids during chromosomal crossover events (or "recombination"). The chance that two genetically linked elements become separated during recombination depends on the amount of sequence between the two elements, and can be calculated into a percentage of likelihood, termed "recombination frequency".

The term "autonomous heavy chain variable domain" refers to a heavy chain variable domain that can fold and bind to epitopes autonomously, i.e., without aggregating and or an associated light chain. "Heavy chain-only" or "HCO" antibodies, shark antibodies, VHH antibodies, camilids, and single domain antibodies are all examples of antibodies that contain an autonomous heavy chain variable domain. Several strategies for producing such antibodies are reviewed in Janssens et al (Proc. Natl. Acad. Sci. 2006 103:15130-5), Brüggemann et al (Crit. Rev. Immunol. 2006 26:377-90), Zou et al (J. Immunol. 2005 175:3769-79) and Nguyen et al (Immunology 2003 109:93-101), for example. An autonomous heavy chain variable domain can be made by introducing camelizing substitutions into the variable domain of a VH antibody.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a". "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a transgenic animal is provided. In certain embodiments, the animal may be any non-human animal that has a relatively small number of light chain genes, or an animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagomorph such as rabbit, or a farm animal such as a cow, sheep, pig or goat.

Some of this disclosure relates to a transgenic chicken containing one or more transgenes. Since the nucleotide sequences of the immunoglobulin loci of many animals are known, as are methods for modifying the genome of such animals, the general concepts described below may be readily adapted to any suitable animal, particularly animals that employ gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17:43-70), Bucchini (Nature 1987 326:409-11), Knight (Adv. Immunol. 1994 56:179-218), Langman (Res. Immunol. 1993 144:422-46), Masteller (Int. Rev. Immunol. 1997 15:185-206), Reynaud (Cell 1989 59:171-83) and Ratcliffe (Dev. Comp. Immunol. 2006 30:101-118). See also US20110055938.

As noted above, a transgenic animal (e.g., a transgenic chicken) that uses gene conversion for antibody diversification is provided. In some embodiments, the B cells of the animal comprise an endogenous immunoglobulin heavy chain locus comprising: (a) a functional immunoglobulin heavy chain gene comprising a nucleic acid encoding a human heavy chain variable domain; and (b) a plurality of pseudogenes that are operably linked to said functional immunoglobulin heavy chain gene and that donate, by gene conversion, nucleotide sequence to the nucleic acid encoding the human heavy chain variable domain of (a), wherein the pseudogenes are upstream or downstream of the functional immunoglobulin heavy chain gene and encode variable domains that have camelizing amino acid substitutions, e.g., up to 10, up to 9, up to 8, up to 7, up to 6, up to 5, up to 4 or up to 3 camelizing amino acid substitutions. For example, in any embodiment, the pseudogenes may encode variable domains have non-hydrophobic residues at one, two, three, four or all five amino acid positions 37, 44, 45, and 47 in the FR2 and, optionally, position 103 of FR4. In some embodiments, all pseudogenes have non-hydrophobic residues at three or four positions selected from positions 37, 44, 45, and 47 (Kabat numbering).

Typical "natural" antibodies from humans and mice are composed of a heavy chain and a light chain. In the absence of the light chain, the heavy chains of these antibodies do not fold properly and they aggregate. "Camelization" refers to a process by which VH domains (which term describes the type of binding domain from humans and mice IgGs are altered so that they are capable of binding to epitopes on their own (i.e., without light chain) and do not aggregate. The term "camelization" has been coined for this process because camelids (e.g., camels, llamas, etc.) produce functional antibodies devoid of light chains of which the single N-terminal domain (VHH) is fully capable of antigen binding. These autonomous heavy chain antibodies have a high stability and solubility. Sharks and other cartilaginous fish also VHH antibodies.

Similar to conventional VH domains, autonomous heavy chain antibodies contain four framework regions (FRs) that form the core structure of the immunoglobulin domain and three complementarity-determining regions (CDRs) that are involved in antigen binding. See, e.g., Conrath et al., Antigen binding and solubility effects upon the veneering of a camel VHH in framework-2 to mimic a VH, J Mol Biol, 2005, 350:112-25. Sequence comparison of human and camelid variable domains led to the process of camelization, which involves the transfer of a few hallmark residues of aggregation-resistant VHH domains to human VH domains. Sec, e.g., Davies et al., 'Camelising' human antibody fragments: NMR studies on VH domains, FEBS Lett, 1994, 339:285-90. For example, a characteristic feature of VHHs is the presence of amino acid substitutions at four FR2 positions (positions 37, 44, 45, and 47; Kabat numbering) that are conserved in conventional VH domains and that are involved in forming the hydrophobic interface with VL domains. Specifically, the sequence of the camelid FR's and that of the human VH3 family were remarkably similar except for three residues (44, 45 and 47) in FR2, of which is usually highly conserved in VH domains. See, e.g., Conrath et al., 2005. These solvent-exposed residues (most of which are hydrophilic in the camelids) are located in the former light chain interface and impede the association with a VL domain. Non-specific binding of VH by its interface for the light chain variable domain (VL) has prevented through amino acid mutations in framework 2 and 4 (Val37F, G44E, L45R, W47G and W103R). See Da Silva et al, Camelized rabbit-derived VH single-domain intrabodies against Vif strongly neutralize HIV-1 infectivity J Mol Biol. 2004 Jul. 9; 340 (3): 525-42. Other strategies for camelization are described in Tanha et al Protein Eng Des Sel. 2006 Improving solubility and refolding efficiency of human V (H) s by a novel mutational approach Nov; 19 (11): 503-9 and Davies et al Single antibody domains as small recognition units: design and in vitro antigen selection of camelized, human VH domains with improved protein stability. Protein Eng. 1996 June; 9 (6): 531-7.

Analogous mutational approaches to humanize VHHs have also been attempted. See, e.g., Conrath et al., 2005. See also Vincke et al., General strategy to humanize a camelid single-domain antibody and identification of a universal humanized nanobody scaffold, J Biol Chem, 2009, 284: 3273-84. Although the increased hydrophilicity of VHHs predominantly relies on the aforementioned changes in the former VL interface, some amino acids at positions that form a slightly hydrophobic patch on conventional VH domains that contacts the CH1 domain are also changed into hydrophilic residues in VHHs. See, e.g., Lesk et al., Elbow motion in the immunoglobulins involves a molecular ball-and-socket joint, Nature, 1988 Sep. 8, 335 (6186): 188-90. See also Muyldermans et al., Sequence and structure of VH domain from naturally occurring camel heavy chain immunoglobulins lacking light chains, Protein Eng, 1994 Sep. 7 (9): 1129-35.

As such, in some embodiments any VH antibody may be camelized by making camelizing amino acid substitutions of any hydrophobic residues at one or more of positions 37, 44, 45, and 47 in the FR2 and, optionally, position 103 of FR4 to a non-hydrophobic residue (Kabat numbering). A camelizing amino acid substitutions may include substitution of any hydrophobic residues glycine (Gly), alanine (Ala), valine (Val), leucine (Leu), isoleucine (Ile), proline (Pro), phenylalanine (Phe), methionine (Met), and tryptophan (Trp) at the one or more positions with a non-hydrophobic residue.

In some embodiments, the camelizing amino acid substitutions are spread throughout the pseudogenes, e.g., where each pseudogene has at least 1, 2 or 3 camelizing mutations (which can be changed to different non-hydrophobic amino acids in each case), but not all possible camelizing mutations. For example, the camelizing substitutions substitutions may include substitution of any hydrophobic residues at one or more of (e.g., 1, 2, 3, or 4) positions 37, 44, 45, and 47 in the FR2 and, optionally, position 103 of FR4 to a non-hydrophobic residue (Kabat numbering). In some embodiments, the camelizing amino acid substitutions include substitution of any hydrophobic residues glycine (Gly), alanine (Ala), valine (Val), leucine (Leu), isoleucine (Ile), proline (Pro), phenylalanine (Phe), methionine (Met), and tryptophan (Trp) at the one or more positions with a non-hydrophobic residue. For example, in one pseudogene, position 37 of FR2 may be a Ser whereas in another pseudogene, position of 37 of FR2 may be an Asp.

In any embodiment, the transgenic animal may be a chicken.

In some embodiments, the nucleic acid encoding the heavy chain variable domain of (a) may comprise a variable (V) segment, diversity (D) segment and a joining (J) segment where, in some embodiments, the heavy chain variable domain of (a) may be encoded by a human germline heavy chain V segment (e.g., the VH3-23 segment), a human germline heavy chain D segment and a human germline heavy chain J segment (e.g., the human JH6 segment). In other embodiments, the heavy chain variable domain of (a) may be from a human monoclonal antibody.

In many embodiments, each pseudogene may encode at least one camelizing amino acid mutation and in many cases each pseudogene may encode several camelizing amino acid mutations. For example, the codons corresponding to any of positions 37, 44, 45, and 47 in the FR2, may encode non-hydrophobic amino acids, and the non-hydrophobic amino acids may vary from position to position within any one pseudogene and from pseudogene to pseudogene. In some embodiments, the pseudogenes comprise V segments only and in other embodiments, the pseudogenes comprise V and D segments only. In some embodiments, the variable domain of (a) and the pseudogenes of (b) comprise CDRs encoded by multiple different VH3 family members, for example, with the exception of up to 10 camelizing substitutions. In some embodiments, the nucleic acid of (a) and the pseudogenes of (b) encode CDRs encoded by multiple different VH3 family members, except for up to 5 camelizing substitutions per pseudogene.

In some embodiments, the sequences that encode FR1, FR2 and FR3 and, optionally FR4, if present, in the pseudogenes of (b) are, combined, at least 90% identical to the combined sequences that encode the corresponding FR1, FR2 and FR3 and, optionally FR4 in the variable domain of (a). For each individual FR in the pseudogenes, the level of sequence identify may be at least 80%, e.g., at least 90% or at least 95% in many cases. In some embodiments, the sequences that encode the CDRs in the pseudogenes of (b) are no more than 90% identical to the sequences that encode the corresponding CDRs in the variable domain of (a). In other words, in some embodiments there may be more diversity in the CDRs encoded by the pseudogenes relative to the FW sequences encoded by the pseudogenes. In these embodiments the pseudogenes can have camelizing amino acids (e.g., non-hydrophobic residue at one, two, three, four or all of amino acid positions 37, 44, 45, and 47 in the FR2 and, optionally, position 103 of FR4).

In some embodiments, the pseudogenes may be less than 400 nt in length, e.g., 300-400 nucleotides in length. In many embodiments, there are up to 30 of said pseudogenes.

The transgenic animal may be heterozygous or homozygous for the immunoglobulin heavy chain locus.

In any embodiment, the endogenous immunoglobulin heavy chain locus may encode a heavy chain that comprises a CH1 deletion. In these embodiments, the genome of the animal may also comprises a light chain immunoglobulin gene that has been knocked out. Alternatively, the genome of the animal may comprises a light chain immunoglobulin gene that encodes a truncated light chain that comprises a constant region but not a variable region.

In any embodiment, the animal may be a chicken. The animal may be homozygous or heterozygous for the locus.

Also provided is a method comprising (a) immunizing a transgenic animal with an antigen; and (b) obtaining from said animal an antibody that specifically binds to said antigen. The antibody may be polyclonal or monoclonal. In these embodiments, the method may further comprise (c) making hybridomas using B cells of the transgenic animal; and (d) screening said hybridomas to identify a hybridoma that produces an antibody that specifically binds to the antigen. Alternatively, the method may comprise (c) screening B cells without making hybridomas to identify a B cell that produces an antibody that specifically binds to the antigen. In any screening method, the method may involve using PCR to amplify at least the heavy chain variable region-encoding nucleic acid from B cells of the transgenic animal, and expressing a recombinant antibody using said amplified nucleic acid.

A monoclonal or polyclonal antibody produced by the transgenic animal is also provided, wherein the antibody is an autonomous heavy chain (AHC) variable domain antibody.

Also provided is a B cell isolated from the animal.

The transgenic animal contains a functional immunoglobulin heavy chain gene that is expressed (i.e., transcribed to produce an mRNA that is subsequently translated) to produce a heavy chain of an antibody, and, operably linked to (which, in the case is chicken and many other species is immediately upstream of) the functional heavy chain gene, a plurality of different pseudogene heavy chain variable regions, where the variable regions of the pseudogenes are operably linked to the functional immunoglobulin heavy chain in that they the alter the sequence of the functional immunoglobulin heavy chain gene by gene conversion (i.e., by substituting a sequence of the functional immunoglobulin heavy chain gene variable region with a sequence of a pseudogene variable region). In the transgenic animal, gene conversion between the functional immunoglobulin heavy chain gene variable region and a pseudogene variable region alters the sequence of the functional immunoglobulin heavy chain gene variable region by as little as a single codon up to the entire length of the variable region. In certain cases a pseudogene variable region may donate the sequence of at least one CDR (e.g., CDR1, CDR2 or CDR3) from a pseudogene variable region in to the variable region of the functional gene. The heavy chains of the antibodies produced by the transgenic animal are therefore encoded by whatever sequence is donated from the pseudogene variable regions into the variable region of the functional heavy chain gene. Since different sequences are donated in different cells of the animal, the antibody repertoire of the animal is determined by which sequences are donated from the pseudogene variable regions to the variable region of the functional gene.

In some embodiments, the framework segments of the human functional gene and the pseudogenes may be identical or near identical to one another, while the CDR segments of the functional gene and the pseudogenes may differ, thereby allowing gene conversion to occur between the CDR segments of the pseudogenes and the germline sequence. Further, the CDRs may vary in length. In certain embodiments, the heavy chain CDR1 may be in the range of 6 to 12 amino acid residues in length, the heavy chain CDR2 may be in the range of 4 to 12 amino acid residues in length, the heavy chain CDR3 may be in the range of 3 to 25 amino acid residues in length, although antibodies having CDRs of lengths outside of these ranges are envisioned.

In some embodiments, the nucleotide sequence and/or amino acid sequence of the introduced transcribed variable region may be human, i.e., may contain the nucleotide and/or amino acid sequence of a human antibody or germline sequence. In these embodiments, both the CDRs and the framework may be human. In other embodiments, the nucleotide sequence and/or amino acid sequence of the introduced transcribed variable region is not human and may instead be at least 80% identical, at least 90% identical, at least 95% or more identical to a human sequence. For example, relative to a human sequence, the introduced transcribed variable region may contain one or more nucleotide or amino acid substitution. Any germline human $V_H$ segments may be the selected from the following sequences: VH1-18, VH1-2, VH1-24, VH1-3, VH1-45, VH1-46, VH1-

58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In some embodiments, part of the heavy chain locus, including the constant region, part of an intron region and the 3'UTR of the functional gene, may be endogenous to the animal and the remainder of the heavy chain locus, including the variable domains of the functional gene, the remainder of the intron and the pseudogenes may be exogenous to the animal, i.e., made recombinantly and introduced into the animal proximal to the constant domain, part intron and 3' UTR in such a way that a functional gene is produced and the pseudogenes are capable of donating sequence to the functional gene by gene conversion. In certain cases the heavy chain locus of the animal may contain, in operable linkage: an intron region, a constant domain-encoding region and a 3' untranslated region, where the intron region, the constant domain-encoding region and the 3' untranslated region are endogenous to the genome of the transgenic animal, and a plurality of pseudogene heavy chain variable regions, where the plurality of pseudogene heavy chain variable regions are exogenous to the genome of the transgenic animal.

In certain embodiments, an antibody produced by a subject transgenic animal may contain an endogenous constant domain and variable domains that are exogenous to the animal. Since an endogenous constant region may be employed in these embodiments, the antibody may still undergo class switching and affinity maturation, which allows the animal to undergo normal immune system development, and mount normal immune responses. In specific embodiments transgenic chickens have three endogenous constant regions in the heavy chain locus encoding IgM, IgY and IgA. During the early stages of B cell development, B cells express IgM. As affinity maturation proceeds, class switching converts the constant region into IgY or IgA. IgY provides humoral immunity to both adults and neonatal chicks which receive about 200 mg of IgY via a reserve deposited into egg yolk. IgA is found primarily in lymphoid tissues (eg. the spleen, Peyer's patches and Harderian glands) and in the oviduct.

The number of introduced pseudogene variable regions present at the light and/or heavy chain locus may vary and, in particular embodiments, may be in the range of 1-50, e.g., 2 to 50 or 10 to 25. In particular embodiments, at least one (e.g., at least 2, at least 3, at least 5, at least 10 or more) of the plurality of pseudogene light chain variable regions may be in reverse orientation relative to the transcribed light chain variable region. Likewise, in particular embodiments, at least one (e.g., at least 2, at least 3, at least 5, at least 10 or more) of the plurality of pseudogene heavy chain variable regions may be in reverse orientation relative to the heavy chain transcribed variable region. In particular embodiments, the plurality of pseudogene variable regions are not in alternating orientations, and in certain cases may contain a series of at least 5 or at least 10 adjacent pseudogene regions that are in opposite orientation relative to the transcribed variable region. In one embodiment, the pseudogene region that is most distal from the transcribed variable region is in the same orientation as the transcribed variable region, and the pseudogene regions between the most distal region and the transcribed variable region are in the reverse orientation relative to the transcribed variable region.

A pseudogene typically contains a sequence of at least 50, at least 100, at least 200 or at least 300 contiguous nucleotides that is at least 80% identical, e.g., at least 85% identical, at least 90% identical or at least 895% identical to sequence in the transcribed region. In some embodiments, the framework sequences in the pseudogene are at least 90% identical to corresponding framework sequences in the functional gene, and the CDRs have less sequence identity.

The above-described transgenic animal may be made by modifying the genome of an animal recombinantly. Methods for producing transgenic animals, e.g., mice and chickens, etc. are known, and, in particular, methods for modifying the genomes of animal that use gene conversion are also known (see, e.g., Sayegh, Vet. Immunol. Immunopathol. 1999 72:31-7 and Kamihira, Adv. Biochem. Eng. Biotechnol. 2004 91:171-89 for birds, and Bosze, Transgenic Res. 2003 12:541-53 and Fan, Pathol. Int. 1999 49:583-94 for rabbits and Salamone J. Biotechnol. 2006 124:469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30:101-118), the above-described animal may be made by routine methods given this disclosure. Methods for making transgenic chickens are known. See, e.g., 8,592,644, U.S. Pat. No. 8,889,662, Collarini et al (Poult Sci. 2015 94:799-803), van de Lavoir (Nature. 2006 441:766-9) and Schusser et al (Proc Natl Acad Sci USA. 2013 110:20170-5.

Also provided is a method for producing antibodies that contain an autonomous heavy chain (AHC) variable domain. In some embodiments this method may comprise: immunizing a transgenic animal as described above with antigen, and, if the antibodies are polyclonal, the method may comprise isolating the antibodies from a bleed from the animal. If the animal is homozygous for the common light chain sequence, then all of the antibodies in the polyclonal antisera should be autonomous heavy chain (AHC) variable domain antibodies. If monoclonal antibodies are desired, then the method may comprise b) making hybridomas using cells of the immunized transgenic animal; c) screening the hybridomas to identify an antigen-specific hybridoma; and d) isolating an antigen-specific antibody from the antigen-specific hybridoma. Alternatively, B cells can be screened.

In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL-related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, cotaxin (cytokine A11), HER2/neu, HER3, HLA-DR, HLA-DR10, HLA ClassII, IgE, GPiib/iiia (integrin), Integrin αVβ3, Integrins α4β1 and α4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFα, DR4, DR5, DR6, VAP-1 (vascular adhesion protein 1) or VEGF, or the like in order to produce a therapeutic antibody.

The antigens can be administered to a transgenic host animal in any convenient manner, with or without an adjuvant, and can be administered in accordance with a predetermined schedule.

In any embodiment the endogenous pseudogenes can be present or absent. For example, if the functional immunoglobulin light chain gene is composed of a human germline sequence then the endogenous chicken pseudogenes can be present or absent. If the endogenous chicken pseudogenes are present they will not contribute any sequence to the functional gene because the sequence identity is too low for gene conversion.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, antibody-producing cells, e.g., spleen cells, may isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al.,. J Immunol Methods 242:159 (2000), and by Burton, Immunotechnology 1:87 (1995), the disclosures of which are incorporated herein by reference.

If the antibody does not already contain human framework regions, the method may further include humanizing the antibody, which method may include swapping the constant domain of the antibody with a human constant domain to make a chimeric antibody, as well as in certain cases humanizing the variable domains of the antibody by e.g., CDR grafting or resurfacing etc. Humanization can be done following the method of Winter (Jones et al., Nature 321:522 (1986); Riechmann et al., Nature 332:323 (1988); Verhocyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including references cited therein.

As such, in addition to the transgenic animal, a method comprising immunizing the transgenic animal with an antigen and obtaining from the transgenic animal an antibody that specifically binds to the antigen is also provided. The method may include making hybridomas using cells of the transgenic animal; and screening the hybridomas to identify a hybridoma that produces an antibody that specifically binds to the antigen. Alternatively B cells can be screened without making hybridomas.

The sequences of the antigen-specific binding regions of antibodies produced by the transgenic animal described above should be relatively straightforward to obtain because, if desired, all or any of the coding sequences for a diversified population of heavy chain variable domains can be amplified from cDNA using a single pair of PCR primers. Because the specificity and affinity of each antibody should be solely determined by the amino acid sequence of the heavy chain variable domain, there is no need to identify or sequence the cognate light chain. As such, the amino acid sequences for antigen-specific heavy chain variable domains should be relatively straightforward to obtain. As noted above, in some cases, B cells or hybridomas may be functionally screened in order to select for cells that express antigen-specific heavy chains. Heavy chain variable domain coding sequences may be amplified from an enriched or unenriched population of B cells (e.g., PBMCs) en masse. If sequences are amplified from an unenriched population of B cells, the sequences encoding antigen-specific variable domains should be identifiable because they are more highly expressed than sequences that are not antigen-specific (due to B cell activation) and because they potentially belong to more variable clades. Moreover, because these heavy chains do not need a specific light chain for binding, there is no need to determine which light chain pairs with which heavy chain before performing follow up work.

EXAMPLES

The following examples are provided in order to demonstrate and further illustrate certain embodiments and aspects of the present invention and are not to be construed as limiting the scope thereof.

Example 1

Construction of Ahc Chickens

Figure 1:
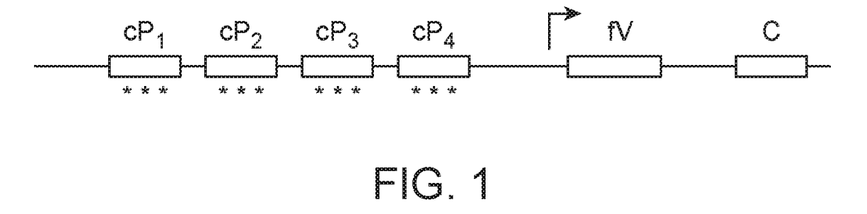
FIG. 1 schematically illustrates an endogenous immunoglobulin heavy chain locus that, in B cells, comprises: (a) a functional immunoglobulin heavy chain gene comprising a nucleic acid encoding a human heavy chain variable domain (the functional variable domain or "fV") that is not an autonomous heavy chain (or camelized) and (b) a plurality of pseudogenes ($cP_1$-$cP_4$) that are operably linked to said functional immunoglobulin heavy chain gene and that donate, by gene conversion, nucleotide sequence to the nucleic acid encoding the human heavy chain variable domain of (a), wherein the pseudogenes are upstream or downstream of the functional immunoglobulin heavy chain gene and encode variable domains that have camelizing amino acid substitutions (indicated by asterisks).
Figure 2:
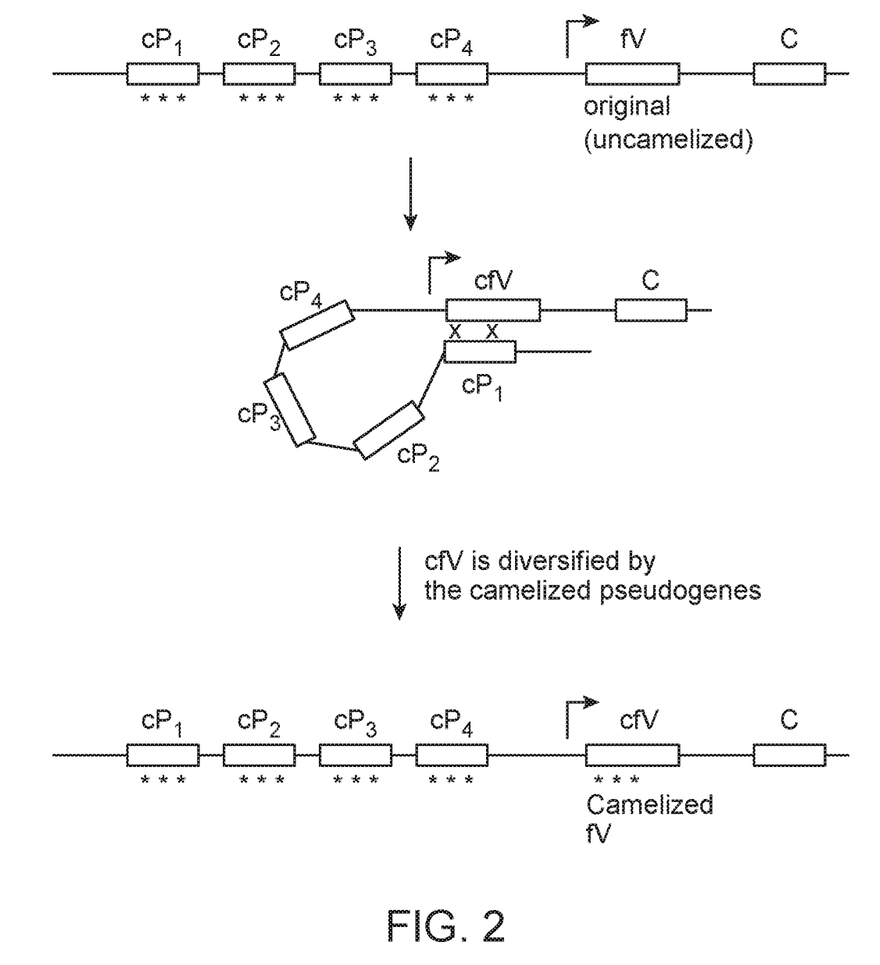
FIG. 2 schematically illustrates how camelizing mutations in a non-camelized functional immunoglobulin heavy chain (fV) can be induced via gene conversion by pseudogenes $cP_1$-$cP_4$ In this example, the functional gene is not camelized and the pseudogenes are camelized. As such, any gene conversion events will add camelizing amino acids to the functional gene. In these constructs, the pseudogenes can be constructed with three framework sequences or four framework sequences.
Figure 3:
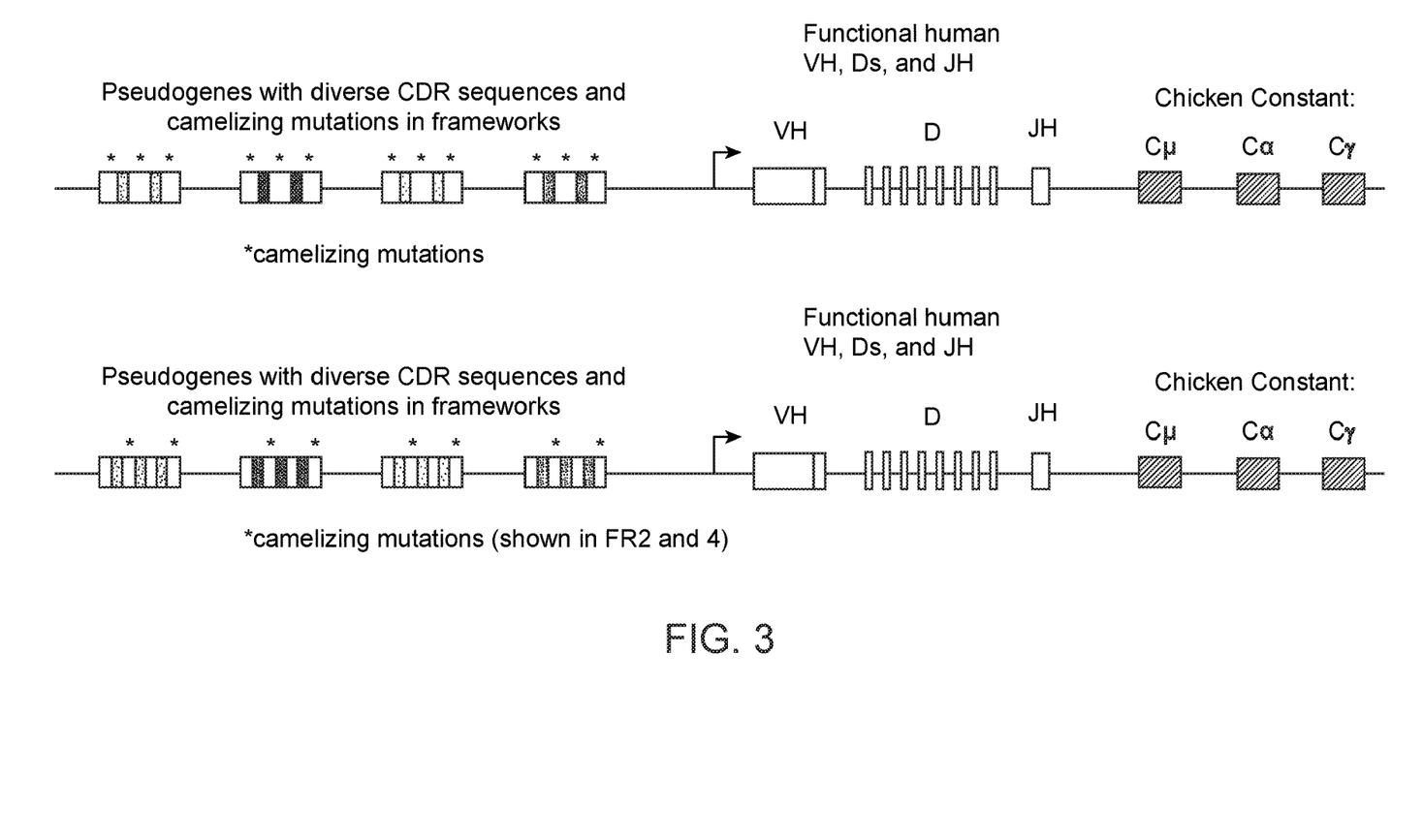
FIG. 3 shows the structure of a chicken heavy chain locus that has been modified to produce a human autonomous heavy chain variable region via gene conversion. As would be recognized, this construct may exist only in non-B cells of the animal since, in B cells, the VH, D and JH regions combine into a single reading frame. In these constructs, the pseudogenes can be constructed with three framework sequences (top) or four framework sequences (bottom).

FIG. 3 shows the structure of a modified chicken heavy chain locus that is designed express a human autonomous heavy chain variable region. The transgene contains a human functional VH gene, the full set of human Ds, and a single JH gene. Upstream, an array of designed human variable region pseudogenes with diversity in CDRs 1 and 2 are shown. The pseudogenes also contain camelizing mutations in the framework regions (*). After VDJ recombination, the functional V region is expressed and splices to the downstream chicken constant regions to make IgM, IgA and IgY, and undergoes gene conversion to incorporate camelizing mutations and diverse CDR sequences.

Figure 4:
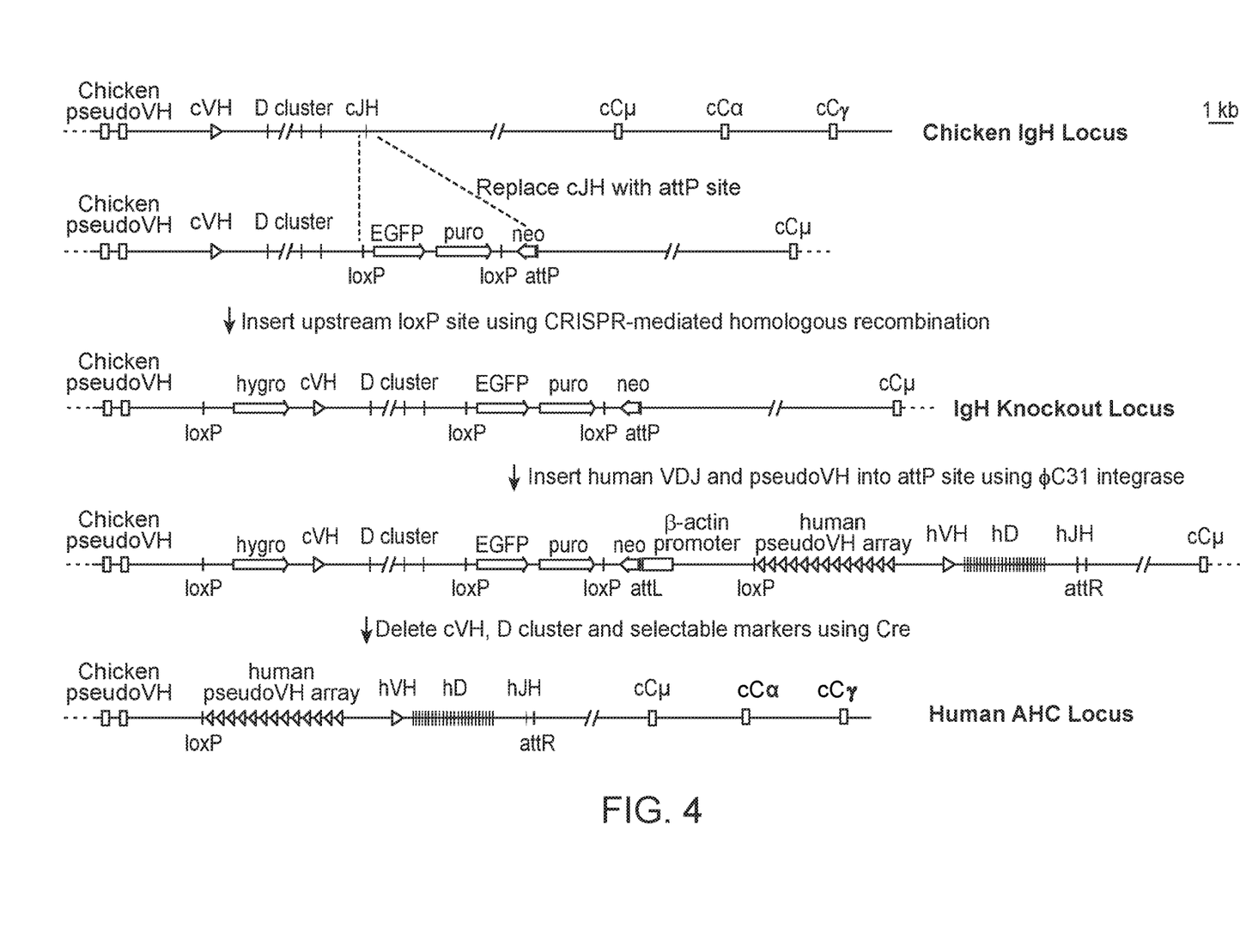
FIG. 4 schematically illustrates how a chicken heavy chain locus that as been modified to express a human autonomous heavy chain variable region can be made.

FIG. 4 schematically illustrates how a chicken heavy chain locus that as been modified to express a human autonomous heavy chain variable region can be made. In this example, the chicken IgH locus was first targeted at the JH gene, to delete JH and replace it with a promoterless neo gene and attP site. Second, a loxP site was inserted by gene targeting to a position upstream of the chicken functional VH gene. Third, the human V, D and J genes encoding the AHC and associated pseudogenes were inserted at the attP site using phiC31 integrase. Fourth, the chicken V gene and D cluster and the selectable marker cassettes were removed by Cre recombination.

What is claimed is:

1. A transgenic chicken, comprising B cells in which the endogenous immunoglobulin heavy chain locus comprises:
   (a) a functional immunoglobulin heavy chain gene comprising a nucleic acid encoding a re-arranged human heavy chain variable domain that does not have any camelizing amino acid substitutions; and
   (b) a plurality of pseudogenes that are operably linked to said functional immunoglobulin heavy chain gene and that donate, by gene conversion, nucleotide sequence to the nucleic acid encoding the human heavy chain variable domain of (a),
   wherein the pseudogenes are upstream or downstream of the functional immunoglobulin heavy chain gene and encode variable domains that comprise CDR and framework regions, wherein the framework regions comprise FR1, FR2 and FR3 regions, and wherein at least the FR2 and, if present, the FR4 regions have camelizing amino acid substitutions;
   wherein the endogenous immunoglobulin heavy chain locus encodes a heavy chain that comprises a CH1 deletion, or the genome of the chicken comprises a light chain immunoglobulin gene that has been knocked out or encodes a truncated light chain that comprises a constant region but not a variable domain; and
   wherein the chicken produces a diversified population of heavy chain-only antibodies.

2. The transgenic animal of claim 1, wherein the camelizing amino acid substitutions are spread throughout the pseudogenes.

3. The transgenic animal of claim 1, wherein the camelizing amino acid substitutions include substitution of any hydrophobic residues at one or more of positions 37, 44, 45, and 47 in the FR2 with a non-hydrophobic residue (Kabat numbering).

4. The transgenic animal of claim 3, wherein the camelizing amino acid substitutions include substitution of any hydrophobic residues glycine (Gly), alanine (Ala), valine (Val), leucine (Leu), isoleucine (Ile), proline (Pro), phenylalanine (Phe), methionine (Met), and tryptophan (Trp) at the one or more positions with a non-hydrophobic residue.

5. The transgenic animal of claim 1, wherein the nucleic acid encoding the heavy chain variable domain of (a) comprises a variable (V) segment, diversity (D) segment and a joining (J) segment.

6. The transgenic animal of claim 5, wherein the heavy chain variable domain of (a) is encoded by a human germline heavy chain V segment, a human germline heavy chain D segment and a human germline heavy chain J segment.

7. The transgenic animal of claim 1, wherein each pseudogene comprises at least one camelizing amino acid substitution.

8. The transgenic animal of claim 1, wherein the pseudogenes comprise V segments only.

9. The transgenic animal of claim 1, wherein the pseudogenes comprise V and D segments only.

10. The transgenic animal of claim 1, wherein the variable domain of (a) and the pseudogenes of (b) comprise CDRs encoded by multiple different VH3 family members.

11. The transgenic animal of claim 1, wherein the nucleic acid of (a) and the pseudogenes of (b) encode CDRs encoded by multiple different VH3 family members, except for up to 5 camelizing substitutions per pseudogene.

12. The transgenic animal of claim 1, wherein the sequences that encode the framework in the pseudogenes of (b) are at least 90% identical to the sequences that encode the corresponding framework sequences in the variable domain of (a).

13. The transgenic animal of claim 1, wherein the pseudogenes are less than 400 nt in length.

14. The transgenic animal of claim 1, wherein the endogenous immunoglobulin heavy chain locus encodes a heavy chain that comprises a CH1 deletion.

15. The transgenic animal of claim 1, wherein the genome of the animal comprises a light chain immunoglobulin gene that has been knocked out.

16. The transgenic animal of claim 1, wherein the genome of the animal comprises a light chain immunoglobulin gene that encodes a truncated light chain that comprises a constant region but not a variable domain.

17. A method comprising:
   (a) immunizing a transgenic animal of claim 1 with an antigen; and
   (b) obtaining from said animal an antibody that specifically binds to said antigen.

18. A B cell isolated from an animal of claim 1.

* * * * *